US008354464B2

(12) United States Patent
Ahn et al.

(10) Patent No.: US 8,354,464 B2
(45) Date of Patent: *Jan. 15, 2013

(54) MIXTURES OF BROMINATED DIPHENYLETHANES, METHOD OF PREPARING THE SAME AND RESIN COMPOSITION USING THE SAME

(75) Inventors: Sung Hee Ahn, Uiwang-si (KR); In Hwan Oh, Uiwang-si (KR); Seong Ho Kong, Uiwang-si (KR); Se Bum Son, Uiwang-si (KR); Sung Duk Hwang, Uiwang-si (KR); Hye Jin Lee, Uiwang-si (KR)

(73) Assignee: Cheil Industries Inc., Gumi-si (KR)

( * ) Notice: Subject to any disclaimer, the term of this patent is extended or adjusted under 35 U.S.C. 154(b) by 453 days.

This patent is subject to a terminal disclaimer.

(21) Appl. No.: 12/632,981

(22) Filed: Dec. 8, 2009

(65) Prior Publication Data
US 2010/0152337 A1 Jun. 17, 2010

(30) Foreign Application Priority Data

Dec. 17, 2008 (KR) ........................ 10-2008-0128826

(51) Int. Cl.
C08J 5/02 (2006.01)
C07C 22/00 (2006.01)
(52) U.S. Cl. ......................... 524/469; 524/466; 570/183
(58) Field of Classification Search .................. 570/183; 524/466, 469
See application file for complete search history.

(56) References Cited

U.S. PATENT DOCUMENTS

| | | | |
|---|---|---|---|
| 4,027,073 A | 5/1977 | Clark | |
| 4,585,818 A | 4/1986 | Jung et al. | |
| 4,994,515 A | 2/1991 | Washiyama et al. | |
| 5,039,729 A * | 8/1991 | Brackenridge et al. | 524/412 |
| 5,055,235 A | 10/1991 | Brackenridge et al. | |
| 5,290,855 A | 3/1994 | Kodama et al. | |
| 5,635,565 A | 6/1997 | Miyajima et al. | |
| 5,712,336 A | 1/1998 | Gareiss et al. | |
| 5,989,723 A | 11/1999 | Tsai et al. | |
| 6,117,371 A | 9/2000 | Mack | |
| 6,447,913 B1 | 9/2002 | Watanabe et al. | |
| 7,288,587 B2 | 10/2007 | Saitou et al. | |
| 2001/0041772 A1 | 11/2001 | Masubuchi et al. | |
| 2005/0137311 A1 | 6/2005 | Muylem et al. | |
| 2007/0049674 A1 | 3/2007 | Kim et al. | |
| 2008/0088961 A1 | 4/2008 | Kushida | |
| 2008/0160240 A1 | 7/2008 | Son et al. | |
| 2008/0221255 A1 | 9/2008 | Ahn et al. | |
| 2010/0029828 A1 | 2/2010 | Ahn et al. | |
| 2010/0041800 A1 | 2/2010 | Son et al. | |
| 2010/0113648 A1 | 5/2010 | Niessner et al. | |
| 2010/0152342 A1 | 6/2010 | Kong et al. | |
| 2010/0168292 A1 | 7/2010 | Son et al. | |
| 2010/0168315 A1 | 7/2010 | Park et al. | |
| 2010/0249314 A1 | 9/2010 | Park et al. | |
| 2011/0160343 A1 | 6/2011 | Son et al. | |

FOREIGN PATENT DOCUMENTS

| | | | |
|---|---|---|---|
| CA | 2058126 A1 | 8/1992 | |
| EP | 0347116 A2 | 12/1989 | |
| EP | 0489912 A1 | 6/1992 | |
| EP | 0502333 A1 | 9/1992 | |
| JP | 01-163243 A | 6/1989 | |
| JP | 01-263149 A | 10/1989 | |
| JP | 01-304153 A | 12/1989 | |
| JP | 05-295196 A | 11/1993 | |
| JP | 05-339479 A | 12/1993 | |
| JP | 06-322200 A | 11/1994 | |
| JP | 08-311300 A | 11/1996 | |
| JP | 10-175893 | * | 6/1998 |
| JP | 2001-139742 | 5/2001 | |
| JP | 14-97374 A | 4/2002 | |
| JP | 2005-272640 A | 10/2005 | |
| JP | 18-111787 A | 4/2006 | |
| JP | 2006-143955 | 6/2006 | |
| JP | 2007-314619 | 12/2007 | |
| KR | 10-1991-0000910 A | 1/1991 | |
| KR | 910008803 B1 | 10/1991 | |
| KR | 10-1994-0026146 A | 12/1994 | |
| KR | 159256 B1 | 1/1999 | |
| KR | 2003-0056039 A | 7/2003 | |
| KR | 10-2004-0022374 A | 3/2004 | |
| KR | 2004-0079118 A | 9/2004 | |
| WO | 90/15103 A1 | 12/1990 | |
| WO | 92/00351 A1 | 1/1992 | |
| WO | 20081082138 A1 | 7/2008 | |
| WO | 2009/084808 A1 | 7/2009 | |

OTHER PUBLICATIONS

Korean Office Action in counterpart Korean Application No. 10-2008-0128826 dated Oct. 18, 2010.
Advisory Action in commonly owned U.S. Appl. No. 12/037,123 mailed on Oct. 18, 2010, pp. 1-3.
International Preliminary Report on Patentability in commonly International Application No l. PCTKR2007/006833 dated Jun. 30, 2009, pp. 1-4.
Office Action in commonly owned U.S. Appl. No. 12/538,266, mailed on Oct. 27, 2010, pp. 1-7.
Office Action in commonly owned U.S. Appl. No. 12/037,123 mailed on Jan. 25, 2010 pp. 1-11.
Final Office Action in commonly owned U.S. Appl. No. 12/037,123 mailed on Jun. 29, 2010, pp. 1-10.

(Continued)

Primary Examiner — Jafar Parsa
(74) Attorney, Agent, or Firm — Summa, Additon & Ashe, P.A.

(57) ABSTRACT

A mixture of brominated diphenylethanes is prepared by brominating diphenylethanes, comprises hexabromodiphenylethane, heptabromodiphenylethane and octabromodiphenylethane, comprises about 55 to about 85% by weight hexabromodiphenylethane, and comprises about 0.01 to about 30% by weight diphenylethanes substituted with an odd number of bromines. The mixture of brominated diphenylethanes can provide improved compatibility with polymer resins, as well as impart excellent flame retardancy and improved weatherability and thermal stability.

11 Claims, No Drawings

OTHER PUBLICATIONS

International Search Report in commonly owned International Application No. PCT/KR2007/006833, dated Mar. 25, 2008, pp. 1-2.
Machine Translation of JP 2005-272640A, downloaded from http://www19.ipd.inpit.go.jp/PA1/cgi-bin/PA1DETAIL, Jun. 23, 2009, pp. 1-13.
Office Action in commonly owned U.S. Appl. No. 12/647,620, mailed on Jan. 31, 2011, pp. 1-10.
Office Action in commonly owned U.S. Appl. No. 12/628,258, mailed on Mar. 24, 2011, pp. 1-22.
Advisory Action in commonly owned U.S. Appl. No. 11/965,013 mailed on May 7, 2010, pp. 1-9.
Final Office Action in commonly owned U.S. Appl. No. 11/965,013, mailed on Jan. 28, 2010, pp. 1-17.
Office Action in commonly owned U.S. Appl. No. 11/965,013, mailed on Jul. 1, 2009, pp. 1-18.
Notice of Allowance in commonly owned U.S. Appl. No. 12/037,123 mailed on Feb. 1, 2011, pp. 1-8.
Chinese Office Action in commonly owned Chinese Application No. 200910166160 dated Nov. 29, 2010, pp. 1-5.
English translation of Chinese Office Action in commonly owned Chinese Application No. 200910166160 dated Nov. 29, 2010, pp. 1-6.
International Search Report in commonly owned International Application No. PCT/KR2008/006528, dated Jun. 1, 2009, pp. 1-4.
Notice of Allowance in commonly owned U.S. Appl. No. 12/538,266 mailed on Feb. 17, 2011, pp. 1-8.
Office Action in commonly owned U.S. Appl. No. 12/512,134, mailed on Apr. 21, 2010, pp. 1-6.
Final Office Action in commonly owned U.S. Appl. No. 12/512,134, mailed on Aug. 27, 2010, pp. 1-5.
Office Action in commonly owned U.S. Appl. No. 12/797,645, mailed on Apr. 22, 2011, pp. 1-7.
BASF, Joncryl ADR-4370-S, Mar. 13, 2007, pp. 1-9.
Villalobos et al., "Oligomeric chain extenders for economic reprocessing and recycling of condensation plastics," ScineceDirect, Energy 31, 2006, pp. 3227-3234.
Office Action in commonly owned U.S. Appl. No. 12/647,601, mailed on Apr. 21, 2011, pp. 1-11.
Notice of Allowance in commonly owned U.S. Appl. No. 12/512,134 mailed on Mar. 8, 2011, pp. 1-5.
Korean Office Action in commonly owned Korean Application No. 2008-128424 dated May 27, 2011, pp. 1-4.
Notice of Allowance in commonly owned U.S. Appl. No. 12/647,620, mailed on Oct. 11, 2011, pp. 1-9.
Final Office Action in commonly owned U.S. Appl. No. 12/647,601 mailed Aug. 8, 2011, pp. 1-6.
Advisory Action in commonly owned U.S. Appl. No. 12/647,601 mailed Nov. 16, 2011, pp. 1-3.
Notice of Allowance in commonly owned U.S. Appl. No. 12/797,645 mailed Aug. 19, 2011, pp. 1-6.
Office Action in commonly owned U.S. Appl. No. 12/884,576 mailed Dec. 22, 2011, pp . 1-8.
Final Office Action in commonly owned U.S. Appl. No. 12/628,258, mailed on Sep. 12, 2011, pp. 1-10.
Notice of Allowance in commonly owned U.S. Appl. No. 12/628,258, mailed on Feb. 6, 2012, pp. 1-7.
Korean Office Action in commonly owned Korean Application No. 2008-128424 dated Oct. 29, 2010, pp. 1-3.
Office Action in commonly owned U.S. Appl. No. 12/613,584, mailed on Jan. 12, 2012, pp. 1-7.
Final Office Action in commonly owned U.S. Appl. No. 12/613,584, mailed on May 31, 2012, pp. 1-8.
Office Action in commonly owned U.S. Appl. No. 12/647,601 mailed May 9, 2012, pp. 1-5.
Final Office ACtion in commonly owned U.S. Appl. No. 12/884,576 mailed May 14, 2012, pp. 1-10.
Notice of Allowance in commonly owned U.S. Appl. No. 12/613,584, mailed On Aug. 6, 2012, pp. 1-5.
Final Office Action in commonly owned U.S. Appl. No. 12/647,601, mailed on Aug. 21, 2012, pp. 1-4.
Notice of Allowance in commonly owned U.S. Appl. No. 12/884,576 mailed Aug. 6, 2012, pp. 1-9.

* cited by examiner

MIXTURES OF BROMINATED DIPHENYLETHANES, METHOD OF PREPARING THE SAME AND RESIN COMPOSITION USING THE SAME

CROSS REFERENCE TO RELATED APPLICATIONS

This application claims priority from Korean Patent Application No. 2008-128826 on Dec. 17, 2008 in the Korean Intellectual Property Office, the disclosure of which is incorporated herein by reference in its entirety.

FIELD OF THE INVENTION

The present invention relates to mixtures of partially brominated diphenylethanes, a method of preparing the same, and a resin composition including the same.

BACKGROUND OF THE INVENTION

Brominated diphenylethane flame retardants can be used as flame retardants for thermoplastic or thermosetting resin compositions which are processed at high temperatures since the brominated diphenylethane flame retardants can exhibit excellent flame retardancy and thermal stability. Further, brominated diphenylethane flame retardants can be used in various products since they can be added in small quantities due to their high bromine content.

Decabromodiphenylethane having ten bromine substituents can be used only with certain polymers because decabromodiphenylethane has a high melting temperature and low compatibility and thus can lower impact strength and reduce the flowability of a thermoplastic resin to which it is added.

Partially brominated diphenylethane compounds can exhibit improved properties as compared to decabromodiphenylethane, such as enhanced compatibility and thus superior impact resistant strength and excellent flowability. However, partially brominated diphenylethane compounds can have very low weatherability as compared with decabromodiphenylethane. Further, a yellowing phenomenon can be generated when using the partially brominated diphenylethane compounds as flame retardants in indoor or outdoor products.

SUMMARY OF THE INVENTION

The present invention is directed to a mixture of brominated diphenylethanes with specific amounts of hexabromodiphenylethane and bromodiphenylethanes substituted with an odd number of bromine atoms (i.e., odd numbered bromodiphenylethanes). The mixture of brominated diphenylethanes can provide excellent flame retardancy and improved weatherability and thermal stability. The mixture of brominated diphenylethanes can also have excellent compatibility with resins and are capable of imparting excellent impact strength, fluidity, and thermal stability to a resin composition.

The present invention further provides a novel method for preparing mixtures of brominated diphenylethanes comprising about 55 to about 85% by weight of hexabromodiphenylethane. The resultant mixtures of brominated diphenylethanes can have excellent thermal stability while minimizing the amount of compounds having an odd number of bromine substituents even when an equal equivalent of bromine is added. The method of preparing mixtures of brominated diphenylethanes can also provide easy control of reaction rate and excellent productivity.

The present invention further provides a resin composition including the mixtures of brominated diphenylethanes as flame retardants. The resin composition can have excellent flame retardancy, weatherability and thermal stability.

The present further provide an article molded from the resin composition.

An aspect of the present invention relates to a mixture of brominated diphenylethanes that can provide improved weatherability. The mixture of brominated diphenylethanes can be prepared by brominating diphenylethanes, can include hexabromodiphenylethane, heptabromodiphenylethane and octabromodiphenylethane, can include about 55 to about 85% by weight hexabromodiphenylethane, based on the total weight of the mixture of brominated diphenylethanes, and can include about 0.01 to about 30% by weight of odd numbered brominated diphenylethanes, based on the total weight of the mixture of brominated diphenylethanes.

In an exemplary embodiment of the present invention, the mixture of brominated diphenylethanes may further comprise pentabromodiphenylethane, nonabromodiphenylethane, decabromodiphenylethane, or a combination thereof.

In another exemplary embodiment, the amount of odd numbered brominated diphenylethanes may be about 1 to about 25% by weight.

In a further exemplary embodiment, the mixture of brominated diphenylethanes may comprise about 57 to about 85% by weight hexabromodiphenylethane.

Specimens with dimensions of about 100 mm×about 100 mm×about 3.2 mm can be obtained by blending the mixture of brominated diphenylethanes with an ABS resin comprising about 19.1% by weight of polybutadiene having a rubber particle diameter of about 0.32 μm, about 57.8% by weight of styrene and about 22.4% by weight of acrylonitrile to prepare a blend comprising about 10% by weight of Br. After irradiating the specimens with xenon arc for about 300 hours in accordance with ASTM D4459, the specimens can exhibit a color difference (ΔE) of about 15 or less when measuring the color of the specimens and comparing the measured color using a Minolta CM-3700D spectrophotometer. In addition, a specimen obtained by allowing the blend to remain in a 10 oz injection machine at a temperature of about 240° C. for about 10 minutes and thereafter injection molding the specimen can exhibit a color difference (ΔE) of about 5 or less as compared with that of a standard product.

Another aspect of the present invention relates to a method of preparing a mixture of brominated diphenylethanes. The method comprises the steps of adding a brominating agent solution to a diphenylethane solution in which a metal or metal salt Lewis acid catalyst is added, and reacting the diphenylethane solution with the brominating agent solution added thereto at a temperature of about −20 to about 50° C., to thereby control the content of hexabromodiphenylethane in the total mixture of brominated diphenylethanes to about 55 to about 85% by weight and to control the content of odd numbered brominated diphenylethanes in the total mixture of brominated diphenylethanes to about 0.01 to about 30% by weight.

In an exemplary embodiment of the present invention, the diphenylethane solution may be prepared by adding diphenylethanes and a metal or metal salt Lewis acid catalyst to a chlorine-based organic solvent.

In another exemplary embodiment, the brominating agent solution may be prepared by adding bromine or bromine chloride to a chlorine-based organic solvent.

In a further exemplary embodiment, the bromine may be added to the diphenylethanes in an amount selected to substitute the diphenylethanes with about 5.5 to about 7.7 moles of Br per mole of diphenylethanes.

Examples of the chlorine-based organic solvent may include without limitation methylene chloride, chloroform, carbon tetrachloride, 1,2-dichloroethane, 1,1,1-trichloroethane, 1,1,2,2-tetrachloroethane, and the like, and combinations thereof.

Examples of the metal or metal salt Lewis acid catalyst may include without limitation Sb, $SbCl_3$, $SbCl_5$, $SbBr_3$, $SbClBr_4$, $SbBrCl_4$, Fe, $FeCl_3$, $FeBr_3$, Al, $AlCl_3$, Ti, $TiCl_4$, $TiBr_4$, Sn, $SnCl_2$, $SnBr_3$, $SnCl_4$, $AlBr_3$, Be, $BeCl_2$, Cd, $CdCl_2$, Zn, $ZnCl_2$, B, $BF_4$, $BCl_3$, $BBr_3$, Bi, $BiCl_3$, Zr, $ZrCl_4$, and the like and combinations thereof.

A further aspect of the present invention relates to a resin composition including the mixture of brominated diphenylethanes as a flame retardant.

In an exemplary embodiment, the resin composition comprises about 100 parts by weight of a polymer resin and about 0.1 to about 50 parts by weight of a mixture of brominated diphenylethanes.

The polymer resin can include a thermoplastic resin. Exemplary thermoplastic resins include without limitation polyolefins, vinyl aromatic polymers, rubber modified vinyl aromatic polymers, rubber modified aromatic vinyl-vinyl cyanide copolymers, aromatic vinyl-vinyl cyanide copolymers, polyvinyl chloride, poly(meth)acrylate, polyester, polyamide, polycarbonate, polyoxides, and the like, and combinations thereof. In another exemplary embodiment, the polymer resin may include a thermosetting resin. Exemplary thermosetting resins include without limitation epoxy resins, unsaturated polyesters, urethane resins, phenolic resins, and the like, and combinations thereof.

The resin composition may further comprise one or more additives, such as a flame retardant, an antimony compound, an anti-dripping agent, a thermal stabilizer, a release agent, a weather resistant stabilizer, a halogen stabilizer, a lubricant, a filler, a photostabilizer, an antioxidant, a coloring agent, an antistatic agent, an impact modifier, and the like, and combinations thereof.

DETAILED DESCRIPTION OF THE INVENTION

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

Mixture of Brominated Diphenylethanes

An aspect of the present invention relates to a mixture of brominated diphenylethanes.

The mixture of brominated diphenylethanes, which can be prepared by partially brominating diphenylethanes, can include hexabromodiphenylethane, heptabromodiphenylethane and octabromodiphenylethane.

Based on an area ratio in a GC/MS analysis, the mixture of brominated diphenylethanes can include hexabromodiphenylethane in an amount of about 55 to about 85% by weight. When hexabromodiphenylethane is included in the foregoing amount, it is possible to obtain excellent weatherability. In other exemplary embodiments, the mixture of brominated diphenylethanes may comprise hexabromodiphenylethane in an amount of about 57 to about 85% by weight, and as another example about 60 to about 85% by weight. In another exemplary embodiment, hexabromodiphenylethane may be included in an amount of about 65 to about 85% by weight. In another exemplary embodiment, hexabromodiphenylethane may be included in an amount of about 70 to about 85% by weight.

The mixture of brominated diphenylethanes according to the present invention limits the content of odd numbered brominated diphenylethanes to a specific range. This is because the odd numbered brominated diphenylethanes can be structurally unstable and thus can result in the deterioration of thermal properties or weatherability and the generation of a resin discoloration phenomenon. In an exemplary embodiment, the mixture of brominated diphenylethanes may comprise about 0.01 to about 30% by weight of the odd numbered brominated diphenylethanes. In other exemplary embodiments, the mixture of brominated diphenylethanes may comprise about 0.01 to about 25% by weight, as another example about 0.01 to about 20% by weight, and as another example about 0.01 to about 17.5% by weight, of the odd numbered brominated diphenylethanes. In another exemplary embodiment, the mixture of brominated diphenylethanes may comprise about 1 to about 25% by weight of the odd numbered brominated diphenylethanes.

The odd numbered brominated diphenylethanes include pentabromodiphenylethane, heptabromodiphenylethane, nonabromodiphenylethane, or a combination of two or more thereof.

The mixture of brominated diphenylethanes of the present invention may further comprise one or more additional bromodiphenylethanes such as pentabromodiphenylethane, nonabromodiphenylethane, decabromodiphenylethane, or a combination thereof.

In an exemplary embodiment, based on an area ratio in a GC/MS analysis, the mixture of brominated diphenylethanes may comprise about 5 to about 15% by weight of pentabromodiphenylethane, about 72 to about 85% by weight of hexabromodiphenylethane, about 2 to about 10% by weight of heptabromodiphenylethane, and about 0.1 to about 3% by weight of octabromodiphenylethane.

In another exemplary embodiment, the mixture of brominated diphenylethanes may comprise about 55 to about 75% by weight of hexabromodiphenylethane, about 11 to about 16% by weight of heptabromodiphenylethane, about 10 to about 20% by weight of octabromodiphenylethane, and about 1 to about 9% by weight of nonabromodiphenylethane.

In a further exemplary embodiment, the mixture of brominated diphenylethanes may comprise about 0.1 to about 3% by weight of pentabromodiphenylethane, about 55 to about 83% by weight of hexabromodiphenylethane, about 7 to about 15% by weight of heptabromodiphenylethane, about 5 to about 20% by weight of octabromodiphenylethane, and about 1 to about 7% by weight of nonabromodiphenylethane.

In a still further exemplary embodiment, the mixture of brominated diphenylethanes may comprise about 0.1 to about 3% by weight of pentabromodiphenylethane, about 55 to about 83% by weight of hexabromodiphenylethane, about 7 to about 15% by weight of heptabromodiphenylethane, about 5 to about 20% by weight of octabromodiphenylethane, about 1 to about 7% by weight of nonabromodiphenylethane, and about 0.01 to about 1% by weight of decabromodiphenylethane.

In a still further exemplary embodiment, the mixture of brominated diphenylethanes may comprise about 55 to about 83% by weight of hexabromodiphenylethane, about 7 to about 17% by weight of heptabromodiphenylethane, about 5 to about 23% by weight of octabromodiphenylethane, about 1 to about 7% by weight of nonabromodiphenylethane, and about 0.01 to about 1% by weight of decabromodiphenylethane.

The average number of bromine atoms substituted in the mixture of brominated diphenylethanes can be for example about 5.5 to about 7.7, and as another example about 6 to about 7.5.

The mixture of brominated diphenylethanes of the present invention can include about 55 to about 85% by weight of hexabromodiphenylethane and about 0.01 to about 30% by weight of odd number brominated diphenylethanes, and can thereby provide excellent weatherability. In an exemplary embodiment, specimens with dimensions of about 100 mm×about 100 mm×about 3.2 mm can be formed by blending the mixture of brominated diphenylethanes with an ABS resin comprising about 19.1% by weight of polybutadiene having an average rubber particle diameter of about 0.32 μm, about 57.8% by weight of styrene and about 22.4% by weight of acrylonitrile to prepare a blend comprising about 10% by weight of Br. After irradiating the specimens with xenon arc for about 300 hours in accordance with ASTM D4459, a color difference (ΔE) of the specimens can be about 15 or less when measuring colors of the specimens and comparing the measured colors using a Minolta CM-3700D spectrophotometer. In an exemplary embodiment, the color difference (ΔE) of the specimens measured in accordance with ASTM D4459 may be about 0.1 to about 14.

Furthermore, the mixture of brominated diphenylethanes of the present invention not only can have excellent thermal stability, but also can lower the content of odd numbered brominated diphenylethanes at an equal bromine equivalent as compared with a conventional mixture of brominated diphenylethanes. In the present invention, a color difference (ΔE) of injected specimens obtained by allowing the blend to remain in a 10 oz injection machine at a temperature of about 240° C. for about 10 minutes and thereafter injection molding the specimen can be about 5 or less as compared with that of a standard product.

Method of Preparing a Mixture of Brominated Diphenylethanes

Another aspect of the present invention relates to a method of preparing a mixture of brominated diphenylethanes. The method comprises the steps of adding a brominating agent solution to a diphenylethane solution in which a metal or metal salt Lewis acid catalyst is added, and reacting the diphenylethane solution with the brominating agent solution added thereto at a temperature of about −20 to about 50° C. to thereby control the amount of hexabromodiphenylethane in the total mixture of brominated diphenylethanes to about 55 to about 85% by weight and control the amount of odd numbered brominated diphenylethanes in the total mixture of brominated diphenylethanes to about 0.01 to about 30% by weight.

In an exemplary embodiment of the present invention, the diphenylethane solution may be prepared by adding diphenylethane and a metal or metal salt Lewis acid catalyst to a chlorine-based organic solvent.

The organic solvent used in the present invention may be a chlorine-based organic solvent. It is not desirable to use a bromine-based organic solvent as the organic solvent since a reactant having not less than about 28% of the total content of pentabromodiphenylethane, heptabromodiphenylethane and nonabromodiphenylethane and a mixture of brominated diphenylethanes comprising not more than about 55% of hexabromodiphenylethane are produced in the synthesis process. Any solvents which dissolve diphenylethanes well and are inert to metal or metal salt Lewis acid, bromine, and bromine chloride may be used as the chlorine-based organic solvent in the present invention. Examples of such solvents may include without limitation methylene chloride, chloroform, carbon tetrachloride, 1,2-dichloroethane, 1,1,1-trichloroethane, 1,1,2,2-tetrachloroethane, and the like, and combinations thereof. The solvents may be used singly or in the form of combinations thereof. Chlorine based aromatic solvents such as chlorobenzene, o,m,p-dichlorobenzene, and the like are not desirable since bromines are not substituted in aromatic nuclei. For example, the organic solvent can be an anhydride in which water is not substantially present. It is not desirable that water be contained in the solvent since the metal or metal salt Lewis acid catalyst reacts with water and is decomposed, which deteriorates the activity of the catalyst. Although the allowable water content of a solvent cannot be specified according to reaction conditions, a solvent having about 0.1% by weight or less of allowable water content may be ordinarily used. In this case, it is necessary to use the metal or metal salt Lewis acid catalyst in a quantity slightly larger than a predetermined quantity.

Any of the types of metal or metal salt Lewis acid catalysts causing a Friedel-Crafts reaction may be used as the metal or metal salt Lewis acid catalyst. Examples of the metal or metal salt Lewis acid catalyst may include without limitation bromides or chlorides of aluminum, iron, zirconium, titanium or antimony, and combinations thereof. Exemplary metal or metal salt Lewis acid catalysts may include without limitation Sb, $SbCl_3$, $SbCl_5$, $SbBr_3$, $SbClBr_4$, $SbBrCl_4$, Fe, $FeCl_3$, $FeBr_3$, Al, $AlCl_3$, Ti, $TiCl_4$, $TiBr_4$, Sn, $SnCl_2$, $SnBr_3$, $SnCl_4$, $AlBr_3$, Be, $BeCl_2$, Cd, $CdCl_2$, Zn, $ZnCl_2$, B, $BF_4$, $BCl_3$, $BBr_3$, Bi, $BiCl_3$, Zr, $ZrCl_4$, and the like, and combinations of two or more thereof. For example, bromides or chlorides of metals such as iron, titanium and antimony, and combinations thereof may be used as a proper catalyst. As another example, Fe, $FeCl_3$, $FeBr_3$ or a combination thereof may be used as the catalyst. Although the amount of the metal or metal salt Lewis acid catalyst added may be readily controlled based on the average number of bromine mole and the yield of bromination reaction, the metal or metal salt Lewis acid catalyst may be used in an amount of about 10% or less based on the weight of diphenylethanes.

The brominating agent solution may be prepared by adding bromine or bromine chloride to a chlorine-based organic solvent.

The aforementioned methylene chloride, chloroform, carbon tetrachloride, 1,2-dichloroethane, 1,1,1-trichloroethane, 1,1,2,2-tetrachloroethane, and the like may be used as the chlorine-based organic solvent.

A bromine, a bromine chloride, or a combination thereof may be used as a brominating agent in the present invention. The bromine and bromine chloride may be selectively used depending on each catalyst. The bromine chloride may be synthesized by well-known methods. For example, the bromine chloride can be produced by dissolving bromine into dichloroethane and then adding and dissolving chlorine gas of the same mole number as bromine into the dissolved solution while cooling the dissolved solution to a temperature of about 10 to about 30° C. The bromine chloride can also be produced by cooling the dissolved solution to a temperature of not higher than about 5° C. than the boiling point of bromine chloride and then adding chlorine gas to the dissolved solution. When producing the bromine chloride, chlorine may be used in excess about 0 to about 5% by mole compared with the mole of bromine.

The brominating agent solution is caused to react by adding the brominating agent solution to a diphenylethane solution in which a metal or metal salt Lewis acid catalyst is added. In the present invention, the brominating agent solution can be dropped while being stirred. The dropping time of the brominating agent solution may be over about 1 to about 24 hours. It is difficult to control reaction conditions since the reaction rate is fast if the dropping time is shorter than one hour. If the dropping time is longer than about 24 hours, however, the process of using the brominating agent solution may not be practical because productivity can deteriorate.

Although the input amount of the brominating agent solution may be controlled according to the intended number of bromine substituents, the input amount of the brominating agent solution can be for example larger by about 0 to about 5% compared with the amount required in the general reaction. In the present invention, bromine can be input in an amount of about 5.5 to about 7.7 moles, for example about 6 to about 7.5 moles, as another example about 6.2 to about 7.2 moles, and as another example about 6.3 to about 7 moles, per mole of the diphenylethanes. As the equivalent of bromine input per mole of the diphenylethanes is increased, heat resistance can improve, but weatherability can be lowered due to an increase in the content of the odd numbered brominated diphenylethanes. The present invention, however, can not only increase thermal stability at the same equivalent by using a specific catalyst and controlling the reaction temperature to a specific temperature range, but also can improve weatherability by lowering the content of the odd numbered brominated diphenylethanes.

In the present invention, the bromination reaction can be carried out at a temperature of about −20 to about 50° C. Color of the mixture of brominated diphenylethanes changes to brown if the reaction temperature is higher than about 50° C. If the reaction is performed at a reaction temperature lower than about 20° C., however, the reaction rate can too slow for practical industrial application. The reaction temperature can be for example about −20 to about 25° C., as another example about −15 to about 20° C., and as another example about −10 to about 15° C. In an exemplary embodiment, the bromination reaction may be carried out at a temperature of about −20 to about 10° C.

In the present invention, the process may further include an aging step for about 1 to about 10 hours to complete the reaction after the dropping step. The aging temperature may be about 0 to about 40° C., for example about 5 to about 30° C.

As the input of the brominating agent solution into a reactor progresses, a reactant is partially formed in a precipitation phase according to the reaction conditions, and the amount of solvent is properly controlled according to the final reaction control and slurry state. In most cases, the solvent may be used in an amount of about 1 to about 10 times the amount of the input diphenylethanes.

In order to remove the metal or metal salt Lewis acid catalyst and bromine or bromine chloride remaining in an organic phase after completing the reaction, the organic phase may be washed with an aqueous alkali solution or alkali sulfate. Further, when a very small amount of halogen remains in the organic phase, non-reacted halogen may be adsorbed and removed by allowing the washed organic phase to pass through an activated carbon layer or adding granular activated carbon to the organic phase. Thereafter, a reactant is filtered or separated into a precipitate and an organic phase by a method such as centrifugal separation, the separated organic phase is added to a large amount of an incompatible solvent such as methanol to separate a precipitate, and the precipitate separated and dried to collect a mixture of brominated diphenylethanes. The method of recovering the mixture of brominated diphenyethanes is not limited to the foregoing method, and other well-known methods may be employed.

The collected mixture of brominated diphenylethanes can be subjected to an additional purification process or used in the obtained state according to a finally obtained state of the mixture.

The bromine content of the mixture of brominated diphenylethanes obtained by the foregoing method may be controlled by controlling the addition amount of the Lewis acid catalyst or reacted bromine or bromine chloride. The bromine content of a prepared compound may be obtained by well-known methods, such as elemental analysis, X-ray fluorescent analysis, and the like.

Resin Composition

A further aspect of the present invention relates to a resin composition using the mixture of brominated diphenylethanes as a flame retardant. The resin composition comprises about 100 parts by weight of a polymer resin and about 0.1 to about 50 parts by weight of a mixture of brominated diphenylethanes. In an exemplary embodiment, the mixture of brominated diphenylethanes may be used in an amount range of about 1 to about 50 parts by weight with respect to about 100 parts by weight of the polymer resin. The mixture of brominated diphenylethanes used in the foregoing amount range can provide a balance of optical physical properties. As another example, the mixture of brominated diphenylethanes may be used in an amount of about 5 to about 45 parts.

The polymer resin may be a thermoplastic or thermosetting resin. Examples of the thermoplastic resin may include without limitation polyolefins, vinyl aromatic polymers, rubber modified vinyl aromatic polymers, rubber modified aromatic vinyl-vinyl cyanide copolymers, aromatic vinyl-vinyl cyanide copolymers, polyvinyl chloride, poly(meth)acrylate, polyesters, polyamides, polycarbonate polyoxides, and the like, and combinations thereof. However, the thermoplastic resins are not necessarily limited thereto. In the present invention, the thermoplastic resin can be used as a structural material and can be a polymer having an atomic mass of about 15,000 daltons or more.

In an exemplary embodiment, the thermoplastic resin may comprise polyethylene, modified polyethylene, polypropylene, modified polypropylene, polystyrene, ABS, HIPS, ABS/SAN blend, poly(meth)acrylate, polyester, polyamide, polyoxide, or a combination thereof.

In another exemplary embodiment, the thermoplastic resin may comprise a styrene-based resin, in which rubber, styrene monomers, alkylester monomers, and/or unsaturated nitrile monomers are mixed, a styrene copolymer resin, in which styrene monomers and unsaturated nitrile monomers are polymerized, or a combination thereof. In an exemplary embodiment, the thermoplastic resin may comprise GPPS, SPS, HIPS, ABS, ASA, SAN, MSAN, or MABS resins, or a combination of two or more thereof.

In another exemplary embodiment, the thermoplastic resin may comprise a polyolefin resin. The polyolefin resin may comprise polyethylene, polypropylene, modified polyolefin which is modified with a glycidyl group or a (meth)acrylate group, or a combination thereof. The polyethylene may be in any form, such as HDPE, LDPE or LLDPE, and may be used in any structure, such as atactic, syndiotactic or isotactic structure. Further, the polyethylene may also be used in the copolymer form of polyolefins with monomers having other ethylenically unsaturated groups.

In a further exemplary embodiment, the thermoplastic resin may comprise poly(2,6-dimethyl-1,4-phenylene)ether, poly(2,6-diethyl-1,4-phenylene)ether, poly(2,6-dipropyl-1,4-phenylene)ether, poly(2-methyl-6-ethyl-1,4-phenylene)

ether, poly(2-methyl-6-propyl-1,4-phenylene)ether, poly(2-ethyl-6-propyl-1,4-phenylene)ether, poly(2,6-diphenyl-1,4-phenylene)ether, copolymer of poly(2,6-dimethyl-1,4-phenylene)ether and poly(2,3,6-trimethyl-1,4-phenylene) ether, copolymer of poly(2,6-dimethyl-1,4-phenylene)ether and poly(2,3,5-triethyl-1,4-phenylene)ether, or a combination thereof.

Furthermore, the thermoplastic resin may comprise a terephthalic acid ester resin, such as polyethylene terephthalate and polybutylene terephthalate, a modified polyester resin such as PETG, or a combination thereof.

Exemplary thermosetting resins may include without limitation epoxy resins, unsaturated polyester, urethane resins, phenolic resins, and the like, and combinations of two or more thereof.

If necessary, the resin composition of the present invention may further comprise one or more additives. Exemplary additives include without limitation flame retardants, antimony compounds, anti-dripping agents, thermal stabilizers, release agents, weather resistant stabilizers, halogen stabilizers, lubricants, filler, photostabilizers, antioxidants, coloring agents, antistatic agents, impact modifiers, and the like, and combinations thereof. The additives may be used singly or in the form of combinations of two or more thereof. Exemplary flame retardants may include without limitation halogen-based flame retardants, bromine-based flame retardants, phosphorous-based flame retardants, and the like, and combinations thereof. Antimony oxide may be used as a flame retarding aid. Exemplary antimony oxides may include without limitation antimony trioxide, antimony pentoxide, and the like, and combinations thereof.

The resin composition of the present invention may be manufactured in the form of pellets by mixing the foregoing components and optionally one or more additives and then melting and extruding the mixture in an extruder. The manufactured pellets may be manufactured into various molded articles using any of a variety of molding methods, such as injection molding, extrusion molding, vacuum molding, and casting molding.

A further aspect of the present invention relates to a molded article obtained by molding the resin composition. In an exemplary embodiment, the molded article may be pellets obtained by extruding the composition, or a molded compound which is not subjected to a hardening step. The molded article can have excellent impact resistance, fluidity, flame retardancy, and the like, and the molded article can be widely used in a variety of products such as but not limited to exterior materials of electric and electronic appliances, computer housings, office machines or equipment housings, and the like.

If the molded article is obtained from an acrylonitrile-butadiene-styrene copolymer (ABS) resin as the polymer resin in the present invention, the specimens can have a color difference ($\Delta E$) of about 15 or less when measured in accordance with ASTM D4459 after being exposed to xenon arc for about 300 hours. Also, a color difference ($\Delta E$) of injected specimens, which are obtained by injecting specimens after allowing the material to stay in a 10 oz injection machine at about 240° C. for about 10 minutes, can be about 5 or less as compared with that of a standard product.

The present invention will be well understood by the following examples. The following examples of the present invention are only for illustrative purposes and are not construed as being limited to the scope of the present invention defined by the appended claims.

EXAMPLES

Examples 1 to 6 and Comparative Examples 1 to 4

Preparation of a Mixture of Brominated Diphenylethanes

Example 1

Preparation of DPE-6

A bromine solution is prepared by injecting about 111 g of dichloroethane and about 195.6 g of bromine into a 500 ml four-neck flask equipped with a thermometer, a stirrer and a cooling tube, and thereafter cooling the mixture to about −5° C. while being stirred. About 156 g of dichloroethane, about 36.4 g of diphenylethane and about 0.91 g of ferric chloride are injected into a 1 L four-neck flask, and the solution is stirred and dissolved form a reaction solution. After dissolving the reaction solution, the bromine solution is dropped into the reaction solution at about 10° C. for about 4 hours, and the reaction solution is heated and aged at about 25° C. for about 2 hours. After about 75% of the bromine solution is dropped into the reaction solution, crystals begin to precipitate, and the reaction solution finally becomes a slurry state.

After completing the reaction, a solvent is distilled from the reaction solution by injecting about 280 g of water and about 0.8 g of hydrazine into a reactor, removing bromine remaining in the reactor, and heating the solution from which bromine is removed. About 124.6 g of an ivory-colored mixture of brominated diphenylethanes (DPE-6) is obtained by distilling and filtering all of the solvent, washing the resulting material with water, and drying it at about 100° C. for about 4 hours. The mixture of brominated diphenylethanes is obtained at a high yield of about 95% with respect to the injected diphenylethane. CG/MS and elemental analysis results of the obtained mixture of brominated diphenylethanes are represented in Table 1. The average number of bromines substituted in the brominated diphenylethanes is 6.

Example 2

Preparation of DPE-6.4

A preparation process is carried out in the same manner as Example 1 except that a bromine solution prepared by injecting about 208.6 g of bromine into about 111 g of dichloroethane is dropped. The prepared mixture of brominated diphenylethanes (DPE-6.4) is about 130.6 g.

Example 3

Preparation of DPE-6.75

A preparation process is carried out in the same manner as Example 1 except that a bromine solution prepared by injecting about 220 g of bromine into about 111 g of dichloroethane is dropped. The prepared mixture of brominated diphenylethanes (DPE-6.75) is about 135.8 g.

Example 4

Preparation of DPE-7

A preparation process is carried out in the same manner as Example 1 except that a bromine solution prepared by injecting about 228.2 g of bromine into about 111 g of dichloroethane is dropped. The prepared mixture of brominated diphenylethanes (DPE-7) is about 139.5 g.

Example 5

Preparation of DPE-7.35

A preparation process is carried out in the same manner as Example 1 except that a bromine solution prepared by injecting about 239.6 g of bromine into about 111 g of dichloroethane is dropped. The prepared mixture of brominated diphenylethanes (DPE-7.35) is about 144.8 g.

Example 6

Preparation of DPE-7.7

A preparation process is carried out in the same manner as Example 1 except that a bromine solution prepared by injecting about 251 g of bromine into about 111 g of dichloroethane is dropped. The prepared mixture of brominated diphenylethanes (DPE-7.7) is about 150.1 g.

Comparative Example 1

Preparation of DPE-5

A preparation process is carried out in the same manner as Example 1 except that a bromine solution prepared by injecting about 163 g of bromine into about 111 g of dichloroethane is dropped. The prepared mixture of brominated diphenylethanes (DPE-5) is about 117.1 g.

Comparative Example 2

Preparation of DPE-8

A preparation process is carried out in the same manner as Example 1 except that a bromine solution prepared by injecting about 260.8 g of bromine into about 111 g of dichloroethane is dropped. The prepared mixture of brominated diphenylethanes (DPE-8) is about 154.51 g.

Comparative Example 3

Preparation of DPE-8.5

A preparation process is carried out in the same manner as Example 1 except that a bromine solution prepared by injecting about 277.1 g of bromine into about 111 g of dichloroethane is dropped. The prepared mixture of brominated diphenylethanes (DPE-8.5) is about 162 g.

Comparative Example 4

Preparation of DPE-9

A preparation process is carried out in the same manner as Example 1 except that a bromine solution prepared by injecting about 293.4 g of bromine into about 111 g of dichloroethane is dropped. The prepared mixture of brominated diphenylethanes (DPE-9) is about 169.5 g.

Comparative Example 5

Preparation of DPE-AlCl$_3$

In order to substitute diphenylethane with 7 bromines, about 36.4 g of diphenylethane is added and dissolved in about 100 ml of methylene bromide contained in a 500 ml four-neck flask equipped with a thermometer, a stirrer and a cooling tube, the dissolved solution is cooled to about 6° C., and about 1.74 g of AlCl$_3$ is added therein. About 224 g of bromine is dropped into the solution while maintaining the solution at a reaction temperature of about 6 to about 8° C. for one hour. After about 61% of bromine is dropped, a solid product begins precipitating, and a yellow reaction mixture is heated to about 18° C. for about 0.3 hour to obtain a brown slurry. The slurry is continuously heated up to a maximum temperature of about 54° C. for about 1.2 hour. Then, about 200 ml of methanol is dropped into the slurry at about 65° C. for about 0.4 hour. At this time, when some drops of methanol are first added, a slurry reactant discolors to white. A white slurry having a high viscosity is cooled, filtered, washed with methanol, and dried in air to obtain about 138.6 g of a reaction product with a yield of about 94.3%. CG/MS and elemental analysis results of the obtained mixture of brominated diphenylethanes are represented in Table 1.

Comparative Example 6

Preparation of DPE-FeBr$_3$

In order to substitute diphenylethane with 7 bromines, about 36.4 g of diphenylethane is added and dissolved in about 100 ml of methylene bromide contained in a 500 ml four-neck flask equipped with a thermometer, a stirrer and a cooling tube, the dissolved solution is cooled to about 8° C., and about 2.08 g of FeBr$_3$ is added therein. About 224 g of bromine is dropped into the solution while maintaining the solution at a reaction temperature of about 8 to about 15° C. for about 0.8 hour. After about 81% of bromine is dropped, a solid product begins precipitating, and a yellow reaction mixture is heated to about 89° C. for about 1.8 hours to obtain a brown slurry. At this time, about 6.2 g of bromine is additionally dropped in order to supplement the lost amount of bromine in a condenser. The reactant is additionally heated to about 87 to about 95° C. for about 1.0 hour, and a theoretic recovery ratio of HBr measured at a trap is about 97.1%.

The obtained mixture is cooled to about 70° C. and is refluxed while dropping about 200 ml of methanol into the mixture for about 0.3 hour. Although the color of the solvent is maintained, small white particles are observed in a reactor through the wall thereof. After the reactant is completely cooled, the reactant is filtered, and then washed until a washing solution is colorless by repeatedly performing the washing process seven to eight times. After drying, about 144.4 g of the reactant is obtained with a yield of about 98.2%.

Compositions for the synthesized mixtures of brominated diphenylethanes are analyzed using GC/MS after completely dissolving given specimens into toluene to a dilution factor of about 2000 (about 0.5 mg/mL) and then filling GC vials with about 1 mL of the dissolved solutions. Agilent 7683 injector, Agilent 7890N Gas Chromatography, and Agilent 5975C Mass Spectroscopy Detector are used as measuring instruments. The respective compositions are measured at an inlet temperature of about 320° C., a split ratio of splitless, and an MS interface temperature of about 280° C. by using a column of DB-5HT having a column flow rate of about 1.0 ml/min according to an oven temperature program of 40° C. (2 min)-40° C./min→200° C.-10° C./min→260° C.-20° C./min→340° C. (2 min). The qualitative analysis is conducted by injecting about 1 μl a sample into a GC/MSD using an auto-sampler. The respective measured compositions are used based on the area. The Br content analysis is performed using an IC and measured by drawing up calibration curves using an IC-500 after injecting an excessive amount of oxygen into the samples and burning them.

TABLE 1

|  |  | Example | | | | | | Comparative Example | | | | | |
| --- | --- | --- | --- | --- | --- | --- | --- | --- | --- | --- | --- | --- | --- |
|  |  | 1 | 2 | 3 | 4 | 5 | 6 | 1 | 2 | 3 | 4 | 5 | 6 |
| Product Name | | Br-6 | Br-6.4 | Br-6.75 | Br-7 | Br-7.35 | Br-7.7 | Br-5 | Br-8 | Br-8.5 | Br-9 | DPE-AlCl$_3$ | DPE-FeBr$_3$ |
| Average number of substituted Br | | 6 | 6.4 | 6.75 | 7 | 7.35 | 7.7 | 5 | 8 | 8.5 | 9 | 7.03 | 7.13 |
| Area ratio in GC (area %) | Light End | — | — | — | — | — | — | — | — | — | — | 1.24 | — |
|  | Br4 | — | — | — | — | 1.5 | — | 18.9 | — | — | — | — | — |
|  | Br5 | 13.6 | 1.6 | 1.4 | 0.9 | 1.9 | — | 64.7 | — | — | — | 1.10 | 0.2 |
|  | Br6 | 79.9 | 83 | 77.6 | 71.2 | 65.7 | 57.4 | 16.4 | 35.4 | 16 | 2 | 48.29 | 36.7 |
|  | Br7 | 6.2 | 13.5 | 13.4 | 13.8 | 12.8 | 15 | — | 16.1 | 17.1 | 7.8 | 15.52 | 28 |
|  | Br8 | 0.3 | 1.9 | 6.6 | 10.7 | 13.5 | 18.2 | — | 30.6 | 41 | 51.2 | 17.15 | 22.5 |
|  | Br9 | — | — | 1 | 3.4 | 4.5 | 8.8 | — | 16.8 | 24.3 | 36.2 | 13.92 | 10.4 |
|  | Br10 | — | — | — | — | 0.1 | 0.6 | — | 1.1 | 1.6 | 2.8 | 2.78 | 2.2 |
| Area % sum of Br5, Br7 and Br9 | | 19.8 | 15.1 | 15.8 | 18.1 | 19.2 | 23.8 | 64.7 | 32.9 | 41.4 | 44 | 30.54 | 38.6 |

As represented in Table 1, Examples 1 to 6 comprising specific amounts of hexabromodiphenylethane and odd numbered brominated diphenylethanes have excellent weatherability and thermal stability. On the other hand, Comparative Examples 1 to 6, in which the amounts of hexabromodiphenylethane are different from about 55 to about 85% by weight and the amounts of the odd numbered brominated diphenylethanes are greater than about 30% by weight, have remarkably lowered weatherability and thermal stability.

Examples 7 to 12 and Comparative Examples 7 to 12

Preparation of Resin Composition

Specifications of the respective components used for the preparation of a resin composition are as follows.

Acrylonitrile-Butadiene-Styrene Copolymer (ABS) Resin (A)

ABS resin SD-0160 (manufactured by Cheil Industries Inc.) comprising about 19.1% by weight of polybutadiene rubber having an average particle diameter of about 0.32 μm, about 57.8% by weight of styrene and about 22.4% by weight of acrylonitrile is used.

Mixtures of Brominated Diphenylethanes (B)

The mixtures of brominated diphenylethanes prepared in Examples 1 to 6 and Comparative Examples 1 to 6 are respectively used.

Antimony Trioxide (C)

Antimony trioxide manufactured by Il Sung Antimony Co., Ltd of the Republic of Korea is used.

Tin-Maleate Based Compounds (D)

Dibutyl tin maleate polymer, TM-600P, manufactured by Songwon Industrial Co., Ltd of the Republic of Korea is used.

Chlorine-Based Compound (E)

Chlorinated polyethylene (CPE) Tyrin 3245P manufactured by DuPont Dow Elastomers of U.S. is used.

Anti-Dripping Agent (F)

TEFLON 7A-J manufactured by DuPont-Mitsui Polychemical Co., Ltd of Japan is used.

Examples 7 to 12 and Comparative Examples 7 to 12

Resin compositions are manufactured into the form of pellets by adding the respective foregoing components in the amounts represented in the following Table 2, and adding about 0.3 part by weight of a hindered phenolic antioxidant Irganox1076 manufactured by Songwon Industrial Co., Ltd of the Republic of Korea, about 0.4 part by weight of a stearic acid-based metallic lubricant SONGSTAB Ca-ST manufactured by Songwon Industrial Co., Ltd, and about 1 part by weight of wax, uniformly mixing the materials in a mixer, and then extruding the mixture by a twin screw extruder. After drying the manufactured pellets at about 80° C. for about 3 hours, specimens having dimensions of about 10 cm×about 10 cm×about 3.2 mm are manufactured by injecting the dried pellets by a 6 oz injection machine under conditions of a molding temperature of about 180 to about 280° C. and a mold temperature of about 40 to about 80° C.

Color differences between a natural colored standard specimen in which pigments or dyestuffs have not been added and specimens which have been exposed to xenon arc for about 300 hours in accordance with ASTM D4459 are measured and represented by ΔE. Colors of the specimens are measured using a Minolta CM-3700D spectrophotometer, and the color difference is determined in accordance with a 1976 CIELAB-based color difference formula by Commission Internationale de l'Eclairage.

Further, specimens with dimensions of about 200 mm×about 50 mm×about 2 mm are manufactured using a 10-oz IDE140ENII injection machine manufactured by LG Industrial Systems Co., Ltd in order to evaluate thermal stability. After performing a molding operation at about 240° C. to thereby continuously mold the resin composition into specimens and then allowing the injected specimens to remain or stay in the injection machine for about 10 minutes, the injection operation is performed again to mold specimens that are discolored due to the stay in the injection machine for about 10 minutes. Color differences between specimens before remaining or staying in the injection machine and specimens first injected from the injection machine after remaining or staying in the injection machine are measured and represented by ΔE. The colors are measured using a Minolta CM-3700d spectrophotometer. Color differences are determined in accordance with a 1976 CIELAB-based color difference formula by Commission Internationale de l'Eclairage.

TABLE 2

|  |  | Example | | | | | | Comparative Example | | | | | |
| --- | --- | --- | --- | --- | --- | --- | --- | --- | --- | --- | --- | --- | --- |
|  |  | 7 | 8 | 9 | 10 | 11 | 12 | 7 | 8 | 9 | 10 | 11 | 12 |
| ABS (A) |  | 100 | 100 | 100 | 100 | 100 | 100 | 100 | 100 | 100 | 100 | 100 | 100 |
| (B) | DPE-6 | 15.2 | — | — | — | — | — | — | — | — | — | — | — |
|  | DPE-6.4 | — | 14.8 | — | — | — | — | — | — | — | — | — | — |
|  | DPE-6.75 | — | — | 14.7 | — | — | — | — | — | — | — | — | — |
|  | DPE-7 | — | — | — | 14.6 | — | — | — | — | — | — | — | — |
|  | DPE-7.35 | — | — | — | — | 14.4 | — | — | — | — | — | — | — |
|  | DPE-7.7 | — | — | — | — | — | 14.3 | — | — | — | — | — | — |
|  | DPE-5 | — | — | — | — | — | — | 16.0 | — | — | — | — | — |
|  | DPE-8 | — | — | — | — | — | — | — | 14.1 | — | — | — | — |
|  | DPE-8.5 | — | — | — | — | — | — | — | — | 14 | — | — | — |
|  | DPE-9 | — | — | — | — | — | — | — | — | — | 13.8 | — | — |
|  | DPE-AlCl$_3$ | — | — | — | — | — | — | — | — | — | — | 14.6 | — |
|  | DPE-FeBr$_3$ | — | — | — | — | — | — | — | — | — | — | — | 14.6 |
| Sb$_2$O$_3$ (C) |  | 6 | 6 | 6 | 6 | 6 | 6 | 6 | 6 | 6 | 6 | 6 | 6 |
| Tin-maleate based compound (D) |  | 0.3 | 0.3 | 0.3 | 0.3 | 0.3 | 0.3 | 0.3 | 0.3 | 0.3 | 0.3 | 0.3 | 0.3 |
| CPE (E) |  | 3 | 3 | 3 | 3 | 3 | 3 | 3 | 3 | 3 | 3 | 3 | 3 |
| Anti-dripping agent (F) |  | 0.2 | 0.2 | 0.2 | 0.2 | 0.2 | 0.2 | 0.2 | 0.2 | 0.2 | 0.2 | 0.2 | 0.2 |
| Weatherability (ΔE) |  | 12.0 | 10.3 | 10 | 10.3 | 13 | 13.5 | 19.4 | 17 | 17.5 | 17.6 | 19.3 | 16.3 |
| Thermal stability (ΔE) |  | 4.2 | 3.8 | 4.0 | 4.2 | 4.7 | 4.9 | 9.2 | 7.5 | 8.2 | 8.3 | 7.1 | 7.9 |

As represented in Table 2, Examples 7 to 12 using mixtures of brominated diphenylethanes of the present invention have excellent weatherability and thermal stability. On the other hand, Comparative Examples 7 to 12 using mixtures of brominated diphenylethanes comprising hexabromodiphenylethane and the odd numbered brominated diphenylethanes in amounts different from the amounts of the present invention have remarkably lowered weatherability and thermal stability.

The present invention provides a mixture of brominated diphenylethanes which can have excellent compatibility with thermoplastic resins and can impart impact strength, fluidity and thermal stability by partially brominating a diphenylethane compound, and a method of preparing the mixture of brominated diphenylethanes which facilitates control of a reaction rate and can provide excellent productivity. Furthermore, the present invention provides a resin composition that can have excellent flame retardancy, weatherability and thermal stability by using the mixture of brominated diphenylethanes as a flame retardant.

It will be apparent that those skilled in the art can make simple modifications and changes thereto within the scope of the invention defined by the claims, and the modifications and changes will be included in the scope of the present invention.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A mixture of brominated diphenylethanes prepared by brominating diphenylethanes, comprising:
   hexabromodiphenylethane, heptabromodiphenylethane and octabromodiphenylethane,
   about 55 to about 85% by weight hexabromodiphenylethane, based on the total weight of the mixture of brominated diphenylethanes, and
   about 0.01 to about 30% by weight odd numbered brominated diphenylethanes, based on the total weight of the mixture of brominated diphenylethanes.

2. The mixture of brominated diphenylethanes of claim 1, further comprising pentabromodiphenylethane, nonabromodiphenylethane, decabromodiphenylethane, or a combination thereof.

3. The mixture of brominated diphenylethanes of claim 1, comprising about 1 to about 25% by weight of the odd numbered brominated diphenylethanes.

4. The mixture of brominated diphenylethanes of claim 1, comprising about 57 to about 85% by weight of hexabromodiphenylethane.

5. The mixture of brominated diphenylethanes of claim 1, wherein the odd numbered brominated diphenylethanes include pentabromodiphenylethane, heptabromodiphenylethane, and nonabromodiphenylethane.

6. The mixture of brominated diphenylethanes of claim 1, wherein a specimen prepared by blending the mixture of brominated diphenylethanes with an ABS resin comprising about 19.1% by weight of polybutadiene having rubber particle diameter of about 0.32 μm, about 57.8% by weight of styrene, and about 22.4% by weight of acrylonitrile so that Br content is about 10% by weight in the specimen has a color difference (ΔE) of about 15 or less measured after irradiating the specimen with xenon arc for about 300 hours in accordance with ASTM D4459 and has a color difference (ΔE) of about 5 or less measured after the specimen remains in a 10 oz injection machine at about 240° C. for about 10 minutes as compared with the color of a standard product.

7. A resin composition, comprising the brominated diphenylethane of claim 1 as a flame retardant.

8. The resin composition of claim 7, comprising about 100 parts by weight of a polymer resin and about 0.1 to about 50 parts by weight of a mixture of brominated diphenylethanes.

9. The resin composition of claim 8, wherein the polymer resin comprises a thermoplastic resin comprising a polyolefin, a vinyl aromatic polymer, a rubber modified vinyl aromatic polymer, a rubber modified aromatic vinyl-vinyl cyanide copolymer, an aromatic vinyl-vinyl cyanide copolymer, polyvinyl chloride, poly(meth)acrylate, a polyester, a polyamide, a polycarbonate, a polyoxide, or a combination thereof.

10. The resin composition of claim 8, wherein the polymer resin comprises a thermosetting resin comprising an epoxy resin, an unsaturated polyester resin, an urethane resin, a phenolic resin, or a combination thereof.

11. The resin composition of claim 7, further comprising an additive comprising a flame retardant, an antimony compound, an anti-dripping agent, a thermal stabilizer, a release agent, a weather resistant stabilizer, a halogen stabilizer, a lubricant, a filler, a photostabilizer, an antioxidant, a coloring agent, an antistatic agent, an impact modifier, or a combination thereof.

* * * * *